(12) United States Patent
Wahlbom et al.

(10) Patent No.: US 7,253,001 B2
(45) Date of Patent: Aug. 7, 2007

(54) **METABOLIC ENGINEERING FOR IMPROVED XYLOSE UTILISATION OF *SACCHAROMYCES CEREVISIAE***

(75) Inventors: Fredrik Wahlbom, Malmö (SE); Marco Sonderegger, Locarno (IT); Uwe Erich Sauer, Zürich (CH)

(73) Assignee: Forskarpatent I SYD AB, Lund (SE)

( * ) Notice: Subject to any disclaimer, the term of this patent is extended or adjusted under 35 U.S.C. 154(b) by 0 days.

(21) Appl. No.: 10/945,027

(22) Filed: Sep. 20, 2004

(65) Prior Publication Data

US 2005/0153411 A1    Jul. 14, 2005

(51) Int. Cl.
*C12P 1/00*   (2006.01)
*C12P 7/06*   (2006.01)
*C12P 21/06*  (2006.01)
*C12N 9/00*   (2006.01)
*C12N 1/16*   (2006.01)
*C12N 15/74*  (2006.01)
*C07H 21/04*  (2006.01)

(52) U.S. Cl. .................. 435/471; 435/254.21; 435/41; 435/183; 435/69.1; 435/483; 536/23.2

(58) Field of Classification Search .................. 435/41, 435/183; 536/23.2
See application file for complete search history.

(56) References Cited

FOREIGN PATENT DOCUMENTS

WO    WO 01/88094    11/2001

*Primary Examiner*—Rebecca E. Prouty
*Assistant Examiner*—Iqbal Chowdhury
(74) *Attorney, Agent, or Firm*—Gauthier & Connors LLP (57) ABSTRACT

The present invention relates to a method for preparing an ethanol producing, xylose utilizing strain of *Saccharomyces cerevisiae* comprising genes for overexpression of xylose reductase, xylitol dehydrogenase and xylulokinase, wherein in addition to said genes for production o phosphoacetyltransferase, and acetaldehyde dehydrogenase are introduced and optionally overexpressed.

3 Claims, 5 Drawing Sheets

METABOLIC ENGINEERING FOR IMPROVED XYLOSE UTILISATION OF SACCHAROMYCES CEREVISIAE

TECHNICAL FIELD

The present invention relates to improved xylose utilisation by recombinant S. cerevisiae.

BACKGROUND OF THE INVENTION

The oil-crisis In the early 1970's started an intense search for an alternative to petrol as automobile fuel. Ethanol emerged as a good candidate since it to a large extent can replace petrol without major changes of combustion engines. It can be produced from renewable, lignocellulosic biomass such as agricultural and forest residues. Unlike petrol, ethanol produced from a renewable resource, does not give a net contribution of carbon dioxide to the atmosphere and would therefore not contribute to global warming. Sweden aims to substitute 15% petroleum-based fuels with fuels derived from renewable resources by 2010 (Kommunikationskommitén, 1996).

Furthermore, ethanol can replace some of the fuel (gasoline) in today's engine without any adjustments at all, or at least very small adjustments.

Lignocellulosic material mainly contains cellulose, hemicellulose and lignin. On average, wood dry-weight consists of 40% cellulose, 18% hemicellulose and 22% lignin (Taherzadeh, et al., 1997). Cellulose is composed of glucose residues while hemicellulose is a heteropolymer consisting of hexoses (mannose and galactose) and pentoses (xylose and arabinose). Lignin is a heterogeneous aromatic polymer made up of phenylpropanoid precursors.

To liberate the fermentable hexoses and pentoses, the lignocellulosic material is hydrolysed (Saddler, et al., 1993; Stenberg, et al., 1998; Tengborg, et al., 1998). During hydrolysis, fermentation-inhibiting substances like phenolics, furan derivatives (furfural and hydroxymethyl furfural) and acids (acetic, formic and levulinic acid) are formed from components in the lignocellulosic material (Larsson, et al., 1999; Palmqvist and Hahn-Hägerdal, 2000a; Palmqvist and Hahn-Hägerdal, 2000b).

Ethanol is a low value product where the raw material accounts for a large fraction of the total cost. Hence efficient utilisation of raw material is of crucial importance for an economically feasible process (Hinman, et al., 1989; von Sivers and Zacchi, 1996). An ideal microorganism to use for the fermentation of lignocellulosic material should i) have a broad substrate range and ferment all sugars to ethanol, preferably with high yield and productivity and ii) survive in a hydrolysate with fermentation inhibitors.

Microorganisms considered for fermentation of lignocellulosic material include Escherichia coli (Moniruzzaman, et al., 1996), Klebsiella oxytoca (Moniruzzaman, et al., 1996), Zymomonas mobilis (Bothast, et al., 1999), Pichia stipitis (Ferrari, et al., 1992) and Saccharomyces cerevisiae (Björling and Lindman, 1989; Olsson and Hahn-Hägerdal, 1993; Moniruzzaman, et al., 1996; Taherzadeh, et al., 1999; Hahn-Hägerdal, et al., 2001). Man has used the yeast S. cerevisiae for baking and production of alcoholic beverages for thousands of years. S. cerevisiae grows anaerobically on glucose (Andreasen and Stier, 1953; Andreasen and Stier, 1954; Visser, et al., 1990) and produces ethanol from glucose with high yield and high productivity (Kolot, 1980). Furthermore, S. cerevisiae is adapted to high ethanol concentrations (Jones, 1989) and has better tolerance towards fermentation inhibitors compared to bacteria (Olsson and Hahn-Hägerdal, 1993) and other yeast (Björling and Lindman, 1989; Olsson and Hahn-Hägerdal, 1993). However, unlike bacteria and several yeast strains (Skoog and Hahn-Hägerdal, 1988), wild-type S. cerevisiae can not utilise pentoses like xylose and arabinose. Still, after the introduction of genes encoding enzymes catalysing steps in initial pentose utilisation, growth and ethanol yield of recombinant S. cerevisiae have been poor. This thesis describes my efforts to analyse xylose utilisation by recombinant S. cerevisiae and Improve its xylose utilisation ability.

Metabolic engineering to improve xylose utilisation in S. cerevisiae

With the introduction of recombinant DNA technology it has become possible to clone genes from one organism and transfer them to another organism, delete genes in the genome and also vary the expression levels of genes. It is thus possible to perform directed modifications of metabolic pathways. This new discipline is called metabolic engineering and has been defined as "*Improvement of cellular activities by manipulation of enzymatic, transport, and regulatory functions of the cell with the use of recombinant DNA technology*" (Bailey, 1991) and "*Purposeful modification of intermediary metabolism using recombinant DNA techniques*" (Cameron and Tong, 1993). Like all classic fields of engineering, metabolic engineering is characterised by an analysis step and a synthesis step (Bailey, 1991; Stephanopoulos, 1994; Nielsen, 1998). In the analysis step, the microorganism is physiologically characterised and evaluated using, for instance, MFA (metabolic flux analysis), enzymatic activity measurements or expression analysis (Nielsen, 2001). The analysis provides information on where genetic modifications may improve the performance of the microorganism. The synthesis step involves the construction of a strain, with genetic modifications based on the analysis, using recombinant DNA technology. The new recombinant strain is then analysed using the same methodology as for its parental strain. If the analysis reveals that further improvement is required, new targets for genetic manipulation are identified followed by a new round of synthesis and analysis.

The Analysis-Genetic design-Synthesis cycle is repeated until the desired property is obtained. Metabolic engineering has been the subject of many reviews (Cameron and Tong, 1993; Nielsen, 2001; Stephanopoulos, 1999). In the following chapters I will focus on how this approach has been applied to generate xylose-utilising strains of S. cerevisiae.

Pathways for Xylose Utilisation

Figure 1:
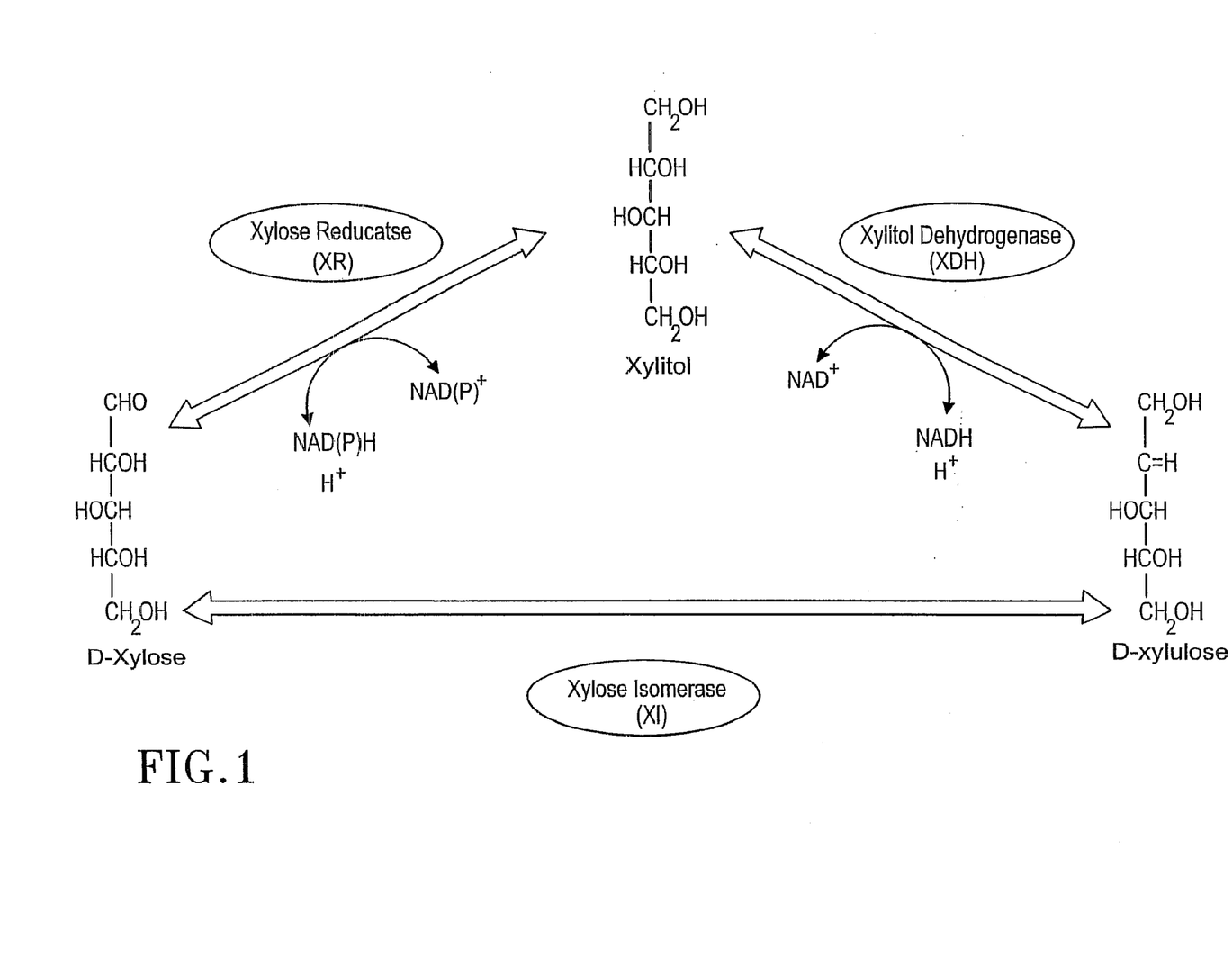
FIG. 1 Xylose and xylulose interconversions in bacteria and yeast. From (Hahn-Hägerdal, et al., 2001).

Xylose utilisation is widespread among bacteria. The initial step in bacterial xylose utilisation is its isomerisation to xylulose by xylose isomerase (XI) (Hochster and Watson, 1954) (FIG. 1). Some species of yeast and filamentous fungi grow on xylose as the sole carbon source. Yeast and filamentous fungi first reduce xylose to xylitol using xylose reductase (XR) and thereafter xylitol is oxidised to xylulose by xylitol dehydrogenase (XDH) (Chiang and Knight, 1960) (FIG. 1).

S. cerevisiae was considered incapable of growth on xylose (Wang and Schneider, 1980) but grew on xylulose (Wang and Schneider, 1980) and produced ethanol from this substrate (Chiang, et al., 1981). It was later found that S. cerevisiae possesses enzymes with XR (Batt, et al., 1986; Kuhn, et al., 1995) and XDH (Batt, et al., 1986; Richard, et al., 1999) activities and consumed low amounts of xylose when co-metabolised with glucose, galactose or ribose (van Zyl, et al., 1989; van Zyl, et al., 1993). Xylulose utilisation suggests a link between xylulose and central metabolism.

The *S. cerevisiae* gene XKS1 encodes the enzyme xylulokinase (XK) (Ho and Chang, 1989; Rodriguez-Pena, et al., 1998), which phosphorylates xylulose to xylulose 5-phosphate. In most organisms xylulose 5-phosphate is metabolised through the pentose phosphate pathway (PPP) (FIG. 2), but some bacteria, notably lactic acid bacteria, possess a phosphoketolase that cleaves xylulose 5-phosphate into glyceraldehyde 3-phosphate and acetyl phosphate. There have been reports on phosphoketolase activity in yeast (Whitworth and Ratledge, 1977; Evans and Ratledge, 1984; Ratledge and Holdsworth, 1985), but yeast probably also use PPP to metabolise xylulose 5-phosphate (Lighthelm, et al., 1988).

Although wild-type *S. cerevisiae* has enzymes that possess the activities of the Initial xylose-utilisation pathway, their activities are too low to allow xylose growth, and therefore *S. cerevisiae* has been transformed with heterologous genes encoding XI and XR/XDH. Xylose isomerases from several bacteria have been cloned and Introduced into *S. cerevisiae* (Ho, et al., 1983; Sarthy, et al., 1987; Amore, et al., 1989; Moes, et al., 1996), but only xylA from the thermophilic bacterium *Thermus thermophilus* generated an active enzyme in *S. cerevisiae* (Walfridsson, et al., 1996). The transformant was able to consume three times more xylose than a control strain. XI from *Thermus thermophilus* has only trace activity at 30° C., while the highest enzymatic activity was obtained at 85° C.

XRs from different microorganisms have been characterised and they share a common feature in their preference for NADPH as a cofactor. The *S. cerevisiae* unspecific aldose reductase having XR activity (Kuhn, et al., 1995) and XR from *Candida utilis* (Bruinenberg, et al., 1983) exclusively use NADPH, while XR from *P. stipitis* (Verduyn, et al., 1985b; Rizzi, et al., 1988) and *Candida tenius* (Neuhauser, et al., 1997) Is also able to use NADH. The ratio of the specific activity of XR from *P. stipitis* using NADH and NADPH separately was approximately 0.65, regardless of the oxygen tension in the medium (Skoog and Hahn-Hägerdal, 1990). *P. tannophilus* produces two isoenzymes of XR, one of which can use both NADH and NADPH while the other is strictly NADPH dependent (Verduyn, et al., 1985a). Oxygenation-limitation favours the enzyme using both cofactors (VanCauwenberge, et al., 1989). Unlike XR, XDH from all microorganisms studied almost only uses NAD$^+$ as cofactor (Bruinenberg, et al., 1983; Bruinenberg, et al., 1984; Richard, et al., 1999; Rizzi, et al., 1989b).

*S. cerevisiae* has been transformed with the *P. stipitis* genes XYL1 and XYL2 coding for XR and XDH, respectively (Kötter and Ciriacy, 1993; Tantirungkij, et al., 1993; Walfridsson, et al., 1995). The choice of *P. stipitis* as the donor organism was based on its capability to utilise NADH in the xylose reduction step. Ethanolic xylose fermentation with recombinant *S. cerevisiae* strains producing XR/XDH has resulted in low ethanol yield and considerable xylitol by-product formation. This has been ascribed to
 (i) insufficient xylose transport,
 (ii) unfavourable thermodynamics in the conversion of xylose to xylulose,
 (iii) cofactor imbalance in the XR/XDH reactions and
 (iv) an underdeveloped PPP.

Xylose Transport

*S. cerevisiae* does not have specific transporters for xylose, which is instead transported through facilitated diffusion by the hexose transporters. These have up to 100 times lower affinity for xylose than for glucose (Kotyk, 1967; Cirillo, 1968; Busturia and Lagunas, 1986; Kötter and Ciriacy, 1993), and therefore xylose is less efficiently transported into the cell when both glucose and xylose are present in the medium. In an anaerobic chemostat cultivation of the recombinant, xylose-utilising *S. cerevisiae* TMB 3001 using glucose and xylose in the feed, the specific uptake of xylose increased with lower dilution rate and higher xylose feed concentration. The residual glucose concentration decreased with lower dilution rate and a lower glucose concentration favoured xylose uptake. Xylose uptake was also less efficient than that of glucose during aerobic fermentation of *S. cerevisiae* TMB 3399 and 3400.

These results suggest that the low affinity for xylose could render the transport step significant control of the metabolic flux. However, one investigation demonstrated a 30 times higher transport capacity for xylose than the actual rate of xylose consumption (Kötter and Ciriacy, 1993), so the impact of xylose transport on the overall flux of xylose is still unclear.

Thermodynamics of Xylose Utilisation

The equilibrium constant for the reduction of xylose to xylitol has been estimated to be $0.575 \times 10^3$ at pH 7 (Rizzi, et al., 1988), and for the subsequent oxidation of xylitol to xylulose the equilibrium constant at pH 7 is $6.9 \times 10^{-4}$ (Rizzi, et al., 1989a). Thus both reactions favour xylitol formation and the thermodynamics of the XDH reaction is unfavourable in the direction of ethanolic fermentation.

It is, however, inappropriate to consider a pathway thermodynamically unfeasible based on the presence of reactions with unfavourable equilibrium constants. According to the second law of thermodynamics, spontaneous processes occur in the direction that increases the overall disorder (or entropy) of the universe. A more convenient criterion for a thermodynamically feasible reaction is a negative Gibbs free energy ($\Delta G$). Consider the single reaction:

$$aA + bB \rightarrow cC + dD \text{ or } cC + dD - bB - aA = 0$$

If we assume that biological systems are dilute solutions and therefore the fugacity and activity coefficients are equal to 1, Gibbs free energy for a chemical reaction, $\Delta G$, is defined as:

$$\Delta G = \Delta G^0 + RT \ln\left(\frac{[C]^c [D]^d}{[A]^a [B]^b}\right)$$

Hence $\Delta G$ is influenced by the standard Gibbs free energy ($\Delta G^\circ$) as well as the concentration of the metabolites involved in the reaction.

An algorithm has been developed to calculate the permitted metabolite concentration range where all reactions in a pathway have a negative $\Delta G$ and hence makes the pathway feasible (Mavrovouniotis, 1993). When this algorithm was applied to the reactions converting xylose into pyruvate using the pathway illustrated in FIG. 2 the reactions between dihydroxyacetone phosphate and 1,3-glyceraldehyde bisphosphate imposed the largest thermodynamic constraints. Since the same reactions were responsible for the largest thermodynamic constraints in glucose conversion to pyruvate (Mavrovouniotis, 1993) it was concluded that xylose conversion to pyruvate does not introduce new thermodynamic bottlenecks. The strongly favourable XR and XK reactions that take place before and after the XDH reaction compensated for the unfavourable thermodynamics of the XDH reaction.

Cofactor Imbalance

Figure 2:
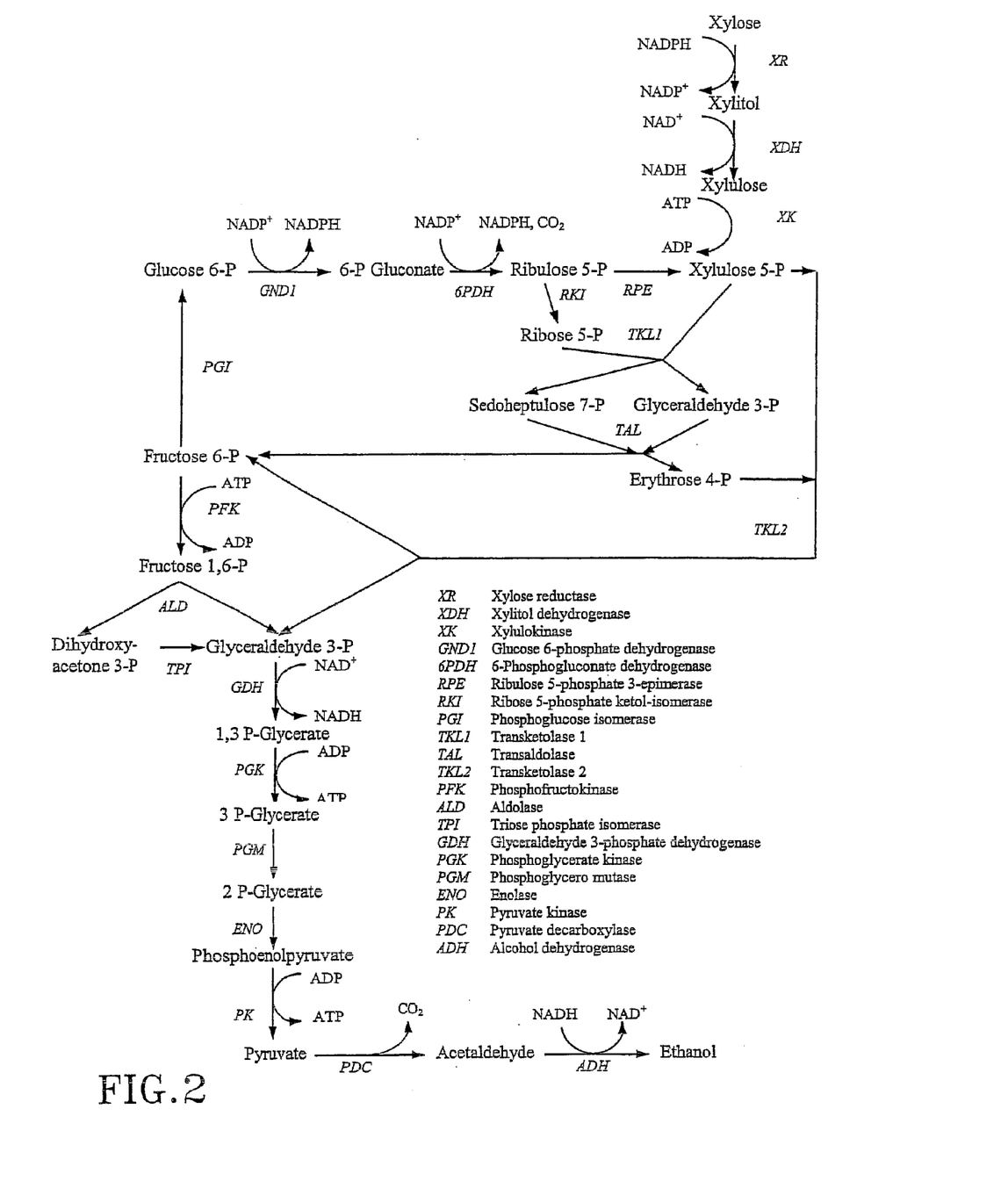
FIG. 2 A metabolic scheme for ethanol formation from xylose.

A cofactor imbalance arises from the fact that the XR reaction preferably consumes NADPH, while the XDH reaction exclusively produces NADH. When less NADH is consumed in the XR reaction, less $NAD^+$ is available for the XDH reaction. Excess NADH generated in the XR/XDH reactions cannot be regenerated to $NAD^+$ by the reaction catalysed by alcohol dehydrogenase (ADH), since this reaction oxidises the NADH formed in the glyceraldehyde 3-phosphate reaction (FIG. 2). If the amount of $NAD^+$ is insufficient, xylitol accumulates and is excreted (Bruinenberg, et al., 1983).

XR and XDH have been subjected to protein engineering (Webb and Lee, 1992; Metzger and Hollenberg, 1995; Zhang and Lee, 1997; Kostrzynska, et al., 1998) to circumvent the cofactor imbalance. Site-directed mutagenesis was used in an attempt to alter the cofactor preference of XR from NADPH to NADH. The resulting enzyme lost 80-90% of its specific activity and the affinity for xylose decreased more than ten-fold (Kostrzynska, et al., 1998). The affinity for NADPH decreased, but remained constant for NADH. Attempts have also been made to alter the cofactor specificity of XDH towards $NADP^+$ instead of $NAD^+$. However, the affinity for $NADP^+$ remained unchanged while the affinity for $NAD^+$ decreased nine-fold and the specific activity of the mutated XDHs decreased to between 50 and 70% of that of the original enzyme (Metzger and Hollenberg, 1995).

The preferences for NADPH in the XR-catalysed reaction and $NAD^+$ in the XDH-catalysed reaction, respectively, might have a thermodynamic origin. In cells of S. cerevisiae grown anaerobically on glucose, the ratio of NADPH to $NADP^+$ is about 5, whereas the ratio of NADH to $NAD^+$ is about 0.15 (Anderlund, et al., 1999). If these ratios are assumed to also be valid for xylose fermentation, using NADPH for xylose reduction and $NAD^+$ for xylitol oxidation, the reactions catalysed by XR and XDH become thermodynamically feasible over a larger range of metabolite concentrations compared with the use of any other combination of cofactors in these reactions.

Metabolic flux analysis of S. cerevisiae TMB 3001 grown anaerobically in chemostat cultivation revealed a flexible utilisation of NADH and NADPH in the XR reaction. The flux of NADPH mediated xylose reduction decreased with increasing dilution rate, while the NADH mediated xylose reduction remained constant. The RNA and protein content of the biomass increased with the dilution rate, which leads to a higher NADPH-demand, and leaves less NADPH for the XR reaction. With increasing xylose concentration in the feed followed a higher flux of xylose reduction using NADH.

The relation in activities between XR, XDH and XK has been manipulated to decrease xylitol formation (Walfridsson, et al., 1997; Eliasson, et al., 2001). A kinetic model based on reported kinetic data for the three enzymes indicated an optimal XR:XDH:XK activity ratio of 1:10:4, which was also confirmed experimentally (Eliasson, et al., 2001). The model also showed that the $NADH/NAD^+$ ratio strongly influenced the optimal ratio. On the other hand, the natural xylose-utilising yeast P. stipitis has higher XR activity than XDH activity under all levels of oxygenation and does not excrete xylitol even during anaerobiosis, (Lighthelm, et al., 1988). It has been demonstrated that P. stipitis strictly uses NADH for xylose reduction during anaerobiosis (Lighthelm, et al., 1988).

NADH is oxidised to $NAD^+$ in the presence of an electron acceptor. When present, oxygen regenerates $NAD^+$ in the electron transport chain. During oxygen-limited cultivation of S. cerevisiae TMB 3001, increased oxygenation led to an approximately constant yield of ethanol, while the yields of glycerol and xylitol decreased (Eliasson, 2001).

Addition of the external electron acceptors acetaldehyde (Ligthelm, et al., 1989) and acetoin (Bruinenberg, et al., 1983; Ligthelm, et al., 1989) to xylose fermentation by the naturally xylose-fermenting yeasts P. tannophilus and C. utilis regenerated $NAD^+$ and prevented extracellular xylitol accumulation. Also in S. cerevisiae TMB 3001 anaerobic xylitol excretion decreased upon acetoin addition and, as with C. utilis, there was a marked increase in the acetate production (Bruinenberg, et al., 1983). Hence, the response of recombinant S. cerevisiae on acetoin addition was similar to that of natural xylose-utilising yeasts. Furfural, which is produced in the pre-treatment of lignocellulosic material (Larsson, et al., 1999) and has been shown to be an inhibitor of ethanolic fermentation by S. cerevisiae (Larsson, et al., 1999; Sanchez and Bautista, 1988; Taherzadeh, et al., 1999) also decreased xylitol formation.

MFA of acetoin addition to S. cerevisiae TMB 3001 cultivated anaerobically on xylose showed an increased flux to ethanol and that NADPH was produced in the conversion of acetaldehyde to acetate instead of in the oxidative PPP. As a consequence, more carbon is channelled through the lower part of glycolysis where ATP is produced. The ATP productivity increased from 0.9 mmol ATP (g biomass h)$^{-1}$ to 1.8 mmol ATP (g biomass h)$^{-1}$, but still no growth was detected. The interpretation of these results was that ATP is not limiting anaerobic growth on xylose of S. cerevisiae TMB 3001.

The Underdeveloped PPP

Recombinant S. cerevisiae, as opposed to the natural xylose-utilising P. stipitis, accumulates the intermediate sedoheptulose 7-phosphate when cultivated on xylose (Kötter and Ciriacy, 1993). It was suggested that S. cerevisiae has an underdeveloped PPP and especially insufficient transaldolase (TAL) activity. Overexpression of TAL gave better growth on xylose, but did not improve ethanol production (Walfridsson, et al., 1995). During anaerobic cultivation of S. cerevisiae TMB 3001 on a mixture of glucose and xylose, the flux between ribulose 5-phosphate and xylulose 5-phosphate was very low at all dilution rates and xylose concentrations. On glucose this reaction proceeds in the direction from ribulose 5-phosphate to xylulose 5-phosphate. Xylose utilisation without xylitol excretion requires this reaction to proceed in the opposite direction, from xylulose 5-phosphate to ribulose 5-phosphate. Overexpression of ribulose 5-phosphate-3-epimerase (RPE) in S. cerevisiae TMB 3001 did not increase the xylose utilisation (Johansson, 2001). Still, this enzyme deserves attention. The S. cerevisiae RPE has a $K_m$ value of 1.5 (Bär, et al., 1996)-2.4 (Kiely, et al., 1973) mM for ribulose 5-phosphate, but there are no reports on its $K_m$ value for xylulose 5-phosphate. If RPE in S. cerevisiae has a significantly lower affinity (=higher $K_m$) for xylulose 5-phosphate than for ribulose 5-phosphate, this would mean a lower specific activity to convert xylulose 5-phosphate to ribulose 5-phosphate and thus decreased xylose utilisation.

Natural xylose utilising organisms might very well have RPEs with higher affinities for xylulose 5-phosphate than the RPE of S. cerevisiae.

DETAILED DESCRIPTION OF THE PRESENT INVENTION

It has now been found possible to improve ethanol production in accordance with the present invention, which method for preparing an ethanol producing, optionally xylose utilizing strain of *Saccharomyces cerevisiae* comprising genes for overexpression of xylose reductase, xylitol dehydrogenase and xylulokinase, is characterized in that in addition to said genes, the genes for production of phosphoacetyltransferase, and acetaldehyde dehydrogenase are introduced and, optionally overexpressed, following a new metabolic pathway for regeneration of $NAD^+$ In a preferred embodiment a gene for production of phosphoketolase is introduced, and optionally overexpressed.

In accordance with a preferred embodiment the genes for production of phosphoketolase, phosphoacetyltransferase (also named phosphotransacetylase), and acetaldehyde dehydrogenase are derived from any procaryotic organism.

In accordance with a further preferred embodiment the gene encoding phosphoketolase is cloned from any heterofermentative lactic acid bacterium, whereby preferably the heterofermentative lactic acid bacterium is selected from the group consisting of *Lactobacillus pentosus, Lactobacillus plantarum*, and *Leuconostoc mesenteroides*.

In accordance with a preferred embodiment genes encoding for phosphate acetyltransferase is cloned from any bacterium that produces ethanol, whereby preferably the genes encoding for phosphate acetyltransferase is cloned from the protozoa *Entamoeba histolytica* and *Glardia lablia*.

In accordance with a further preferred embodiment the gene(-s) encoding for acetaldehyde dehydrogenase are cloned from any bacterium that produce ethanol, or acetaldehyde dehydrogenase (acylating) can be added as such.

In a preferred embodiment the gene encoding for acetaldehyde dehydrogenase is cloned from *Entamoeba histolytica*.

A further aspect of the invention encompasses the use of recombinant yeast prepared in accordance with the invention, for the production of ethanol optionally containing xylose in growth medium.

A New Metabolic Pathway for Regeneration of $NAD^+$

Figure 3:
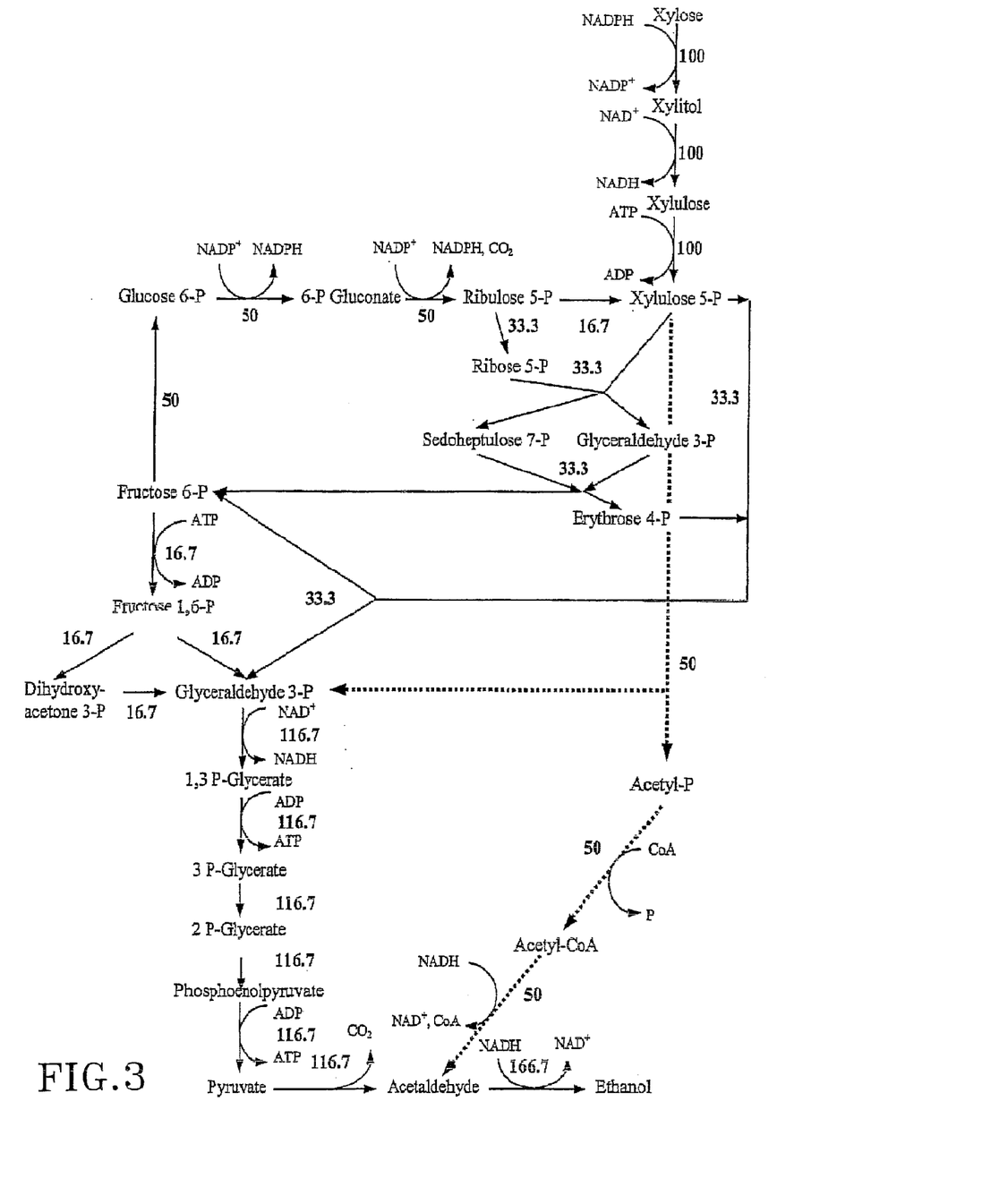
FIG. 3 Redox-neutral conversion of xylose to ethanol using phosphoketolase, acetyl transferase and acetaldehyde dehydrogenase (indicated by dotted lines).
Figure 4:
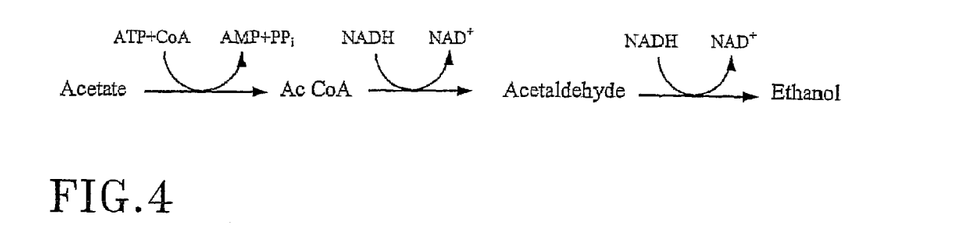
FIG. 4. Acetate reduction to ethanol using an acylating acetaldehyde dehydrogenase.

In XR- and XDH-producing, recombinant *S. cerevisiae* strains, the regeneration of $NAD^+$ is the key to xylose conversion to ethanol without by-product formation of glycerol or xylitol. As discussed in previous sections, investigators have tried to regenerate $NAD^+$ in the XR-catalysed reaction by increasing the affinity for NADH of XR or by the addition of external electron acceptors, the reduction of which consumes NADH. An ideal xylose-utilising pathway allows strict utilisation of NADPH for XR and regenerates $NAD^+$ for the XDH reaction elsewhere in the metabolism, so no external electron acceptors are required. This can be achieved by incorporating parts of the phosphoketolase pathway into *S. cerevisiae* (FIG. 3). If genes encoding phosphoketolase (E.C 4.1.2.9), phosphate acetyltransferase (E.C 2.3.1.8) and acetaldehyde dehydrogenase (acylating) (E.C. 1.2.1.10) are transformed into *S. cerevisiae*, excessive NADH can be regenerated into $NAD^+$.

In the extreme case of a strictly NADPH-utilising XR, one third of the xylulose 5-phosphate is cleaved to glyceraldehyde 3-phosphate and acetyl-phosphate. Glyceraldehyde 3-phosphate is redox neutrally converted to ethanol, while acetyl-phosphate is first converted to acetyl coenzyme A, which is further converted to acetaldehyde and ethanol using one NADH in each step. The thermodynamics of the phosphoketolase reaction (Thauer, et al., 1977), acetyl transferase (Rado and Hoch, 1973) and alcohol dehydrogenase (Burton, 1974) reaction are favourable towards product formation. Using this pathway, the ATP yield is 1.17 mol ATP mol $xylose^{-1}$ compared with the theoretical maximum yield of 1.67 mol ATP mol $xylose^{-1}$. The ethanol yield is, however, the theoretical maximum, 1.67 mol ethanol mol $xylose^{-1}$, or 0.51 g ethanol g $xylose^{-1}$. In addition to regenerating $NAD^+$, the introduction of this pathway serves as an alternate route to the PPP for xylose utilisation. Possible limitations in the non-oxidative PPP would thus be less pronounced.

In this hypothetical phosphoketolase pathway, NADH formed as a result of the cofactor imbalance in the XR/XDH reactions, but also NADH formed from amino acid biosynthesis (Jones and Fink, 1982), can be regenerated to form $NAD^+$. Glycerol production could then be eliminated in glucose fermentation to ethanol, thereby increasing the yield and profitability of the ethanolic fermentation process.

Phosphoketolase has been reported to be essential for successful growth of yeast on xylose (Evans and Ratledge, 1984a), but the redox neutrality is only obtained in combination with an acylating acetaldehyde dehydrogenase. An additional effect of the expression of this enzyme is the possibility of converting extracellular acetate into ethanol (FIG.). Acetate is converted to acetyl coenzyme A by ACS1 (De Virgilio, et al., 1992) and ACS2 (Van den Berg and Steensma, 1995) and could thereafter be reduced to ethanol, as was described above. One mol of $NAD^+$ is regenerated at the cost of one mol of ATP. Since one mol of extra $NAD^+$ would enable the assimilation of one mol of xylitol that can give 1.67 mol ATP (FIG. 3), the net gain for the cell is 0.67 mol ATP. Furthermore, the beneficial effect of expressing an acylating acetaldehyde dehydrogenase is two-fold. Due to the regeneration of $NAD^+$, less xylitol is excreted and the ethanol yield increases, and furthermore, acetate, which is present in lignocellulosic hydrolysate (Larsson, et al., 1999) and considered an inhibitor (Larsson, et al., 1999), is reduced and the hydrolysate is thereby detoxified.

To generate this new metabolic pathway in *S. cerevisiae*, acetaldehyde dehydrogenase (acylating) from *Lactococcus lactis* (Bolotin, et al., 2001) (GenBank accession number AE006444) and *Clostridium acetobutylicum* (Toth, et al., 1999) (accession number AF132754) and the putative phosphoketolase gene from *Schizosaccharomyces pombe* (accession number AL031786) were amplified with PCR (FIG. 5) and cloned into multicopy vectors under the control of a strong GPD promoter (Mumberg, et al., 1995). *S. cerevisiae* was transformed with the plasmids, but in neither case the corresponding enzymatic activity could be detected.

Both acetaldehyde dehydrogenases were of bacterial origin and the lack of activity could be due to different codon usage, proteolytic degradation or incorrect post-translational modification in *S. cerevisiae*. Phosphoketolase from *Bifidobacterium lactis* has been cloned and sequenced (Melle, et al., 2001). A similar sequence (37% amino acid identity) has been found in the yeast *Schizosaccharomyces pombe* and is designated a "putative phosphoketolase". The decision to clone the putative phosphoketolase gene from *S. pombe* instead of *B. lactis* was based on the previously failed attempts to clone the bacterial acetaldehyde dehydrogenases. In *S. cerevisiae* there is no sequence similar to the gene encoding *B. lactis* phosphoketolase, but the putative phosphoketolase sequence from *S. pombe* shows 28% homology with the gene product encoding transketolase 2 (TKL2) in *S. cerevisiae*. Thus, the putative phosphoketolase gene in *S. pombe* might be a transketolase. Further studies must be undertaken to demonstrate the feasibility of this pathway.

Random Mutagenesis

In theory, the concept of metabolic engineering is simple and straightforward: analyse the metabolic pathway of your microorganism, target gene(s) for overexpression/deletion, create the recombinant strain and evaluate it (Nielsen, 2001). Repeat the procedure if the goal has not been achieved. In reality, the success of metabolic engineering is highly dependent on correct identification of the gene targeted for deletion/overexpression, correct expression and folding of heterologous proteins and the correct localisation of an overexpressed protein (Bailey, et al., 1996). The acetaldehyde dehydrogenase enzymes from *L. lactis* and *C. acetobutylicum* and the putative phosphoketolase from *S. pombe* did not show any activity in *S. cerevisiae* [Section 2.6]. Furthermore, xylose isomerases from numerous bacteria have been cloned and introduced in *S. cerevisiae* (Ho, et al., 1983; Amore, et al., 1989; Sarthy, et al., 1987), and only one has been reported to show low enzymatic activity (Walfridsson, et al., 1996). Disappointing results may occur although gene expression has been successful. Overexpression of individual genes in the lower glycolysis in *S. cerevisiae* succeeded in increasing the activity of the corresponding enzymes, but did not improve the growth rate on glucose as was anticipated (Schaaff, et al., 1989). However, although the results were not as expected, they can still be of importance.

Before the introduction of modern DNA technology, random mutagenesis and subsequent selection were used to improve industrially important microorganisms. Random mutagenesis in combination with a selection pressure has been a prerequisite not only for the evolution of microorganisms, but also for all species on earth. If a mutation leads to an improved capacity to survive in a given environment, individuals bearing the mutation will eventually outcompete individuals who do not have the mutation. The performance of microorganisms can also be improved by long-term adaptation in a chemostat, without the addition of mutagenic agents (Brown and Oliver, 1982; Aarnio, et al., 1991). The use of variation combined with selection as a method to improve the characteristics of a microorganism is called evolutionary engineering (Butler, et al., 1996) and has been the subject of a recent review (Sauer, 2001).

Metabolic engineering and evolutionary engineering should not be regarded as competing technologies, but rather as complements to each other. With metabolic engineering it is possible to make jumps in evolution and replace a large number of mutations. Assume that you want to introduce a xylose reductase into *S. cerevisiae* and no similar sequence is known (this is not true for *S. cerevisiae* since some aldose reductases possess XR activity (Kuhn, et al., 1995)). The number of possible sequences increases exponentially with the information units, (4 nucleotides for DNA) and the sequence length (954 bp for XR (Hallborn, et al., 1991)) (Sauer, 2001). To obtain a specific XR gene through random mutation, $4^{954}$ mutations have to take place! in reality, the number of mutations required is lower since the amino acid residues that build up the enzyme are normally coded for by several codons. Furthermore, about ¼ of the nucleotides will be randomly correct from the beginning.

In the following sections, it is described how random mutagenesis in combination with metabolic engineering has generated strains of *S. cerevisiae* with improved xylose utilisation and the ways in which the mutated strains differ from the parental strains. Random mutagenesis in combination with metabolic engineering led to the development of a strain with superior xylose-utilising capacity, which allowed the thorough characterisation of the growth of *S. cerevisiae* TMB 3400 on xylose.

Figure 5:
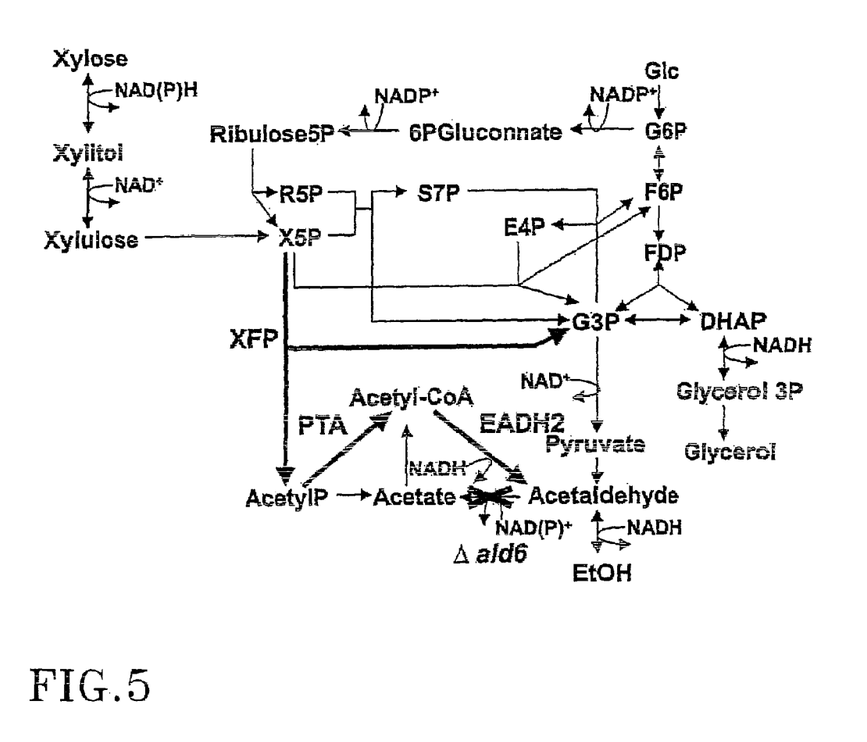
FIG. 5 Phosphoketolase-phosphotransacetylase-acetaldehyde dehydrogenase pathway integrated into the yeast xylose catabolism. XFP: Phosphoketolase; PTA: Phosphotransacetylase; EADH2: Acetaldehyde dehydrogenase; ΔLD6: Aldehyde dehydrogenase, cytosolic (NADP).
Figure 6:
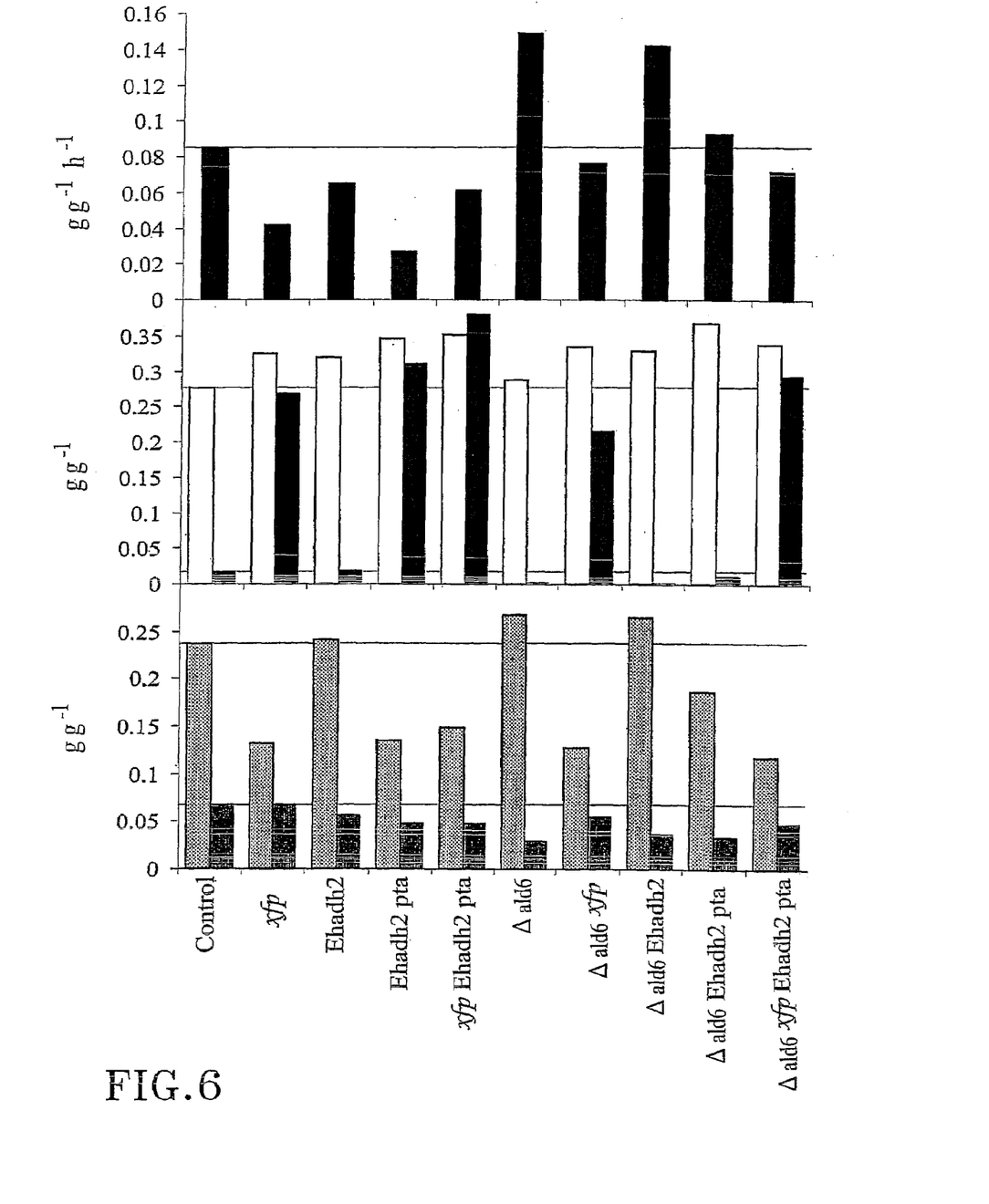
FIG. 6. Effects on xylose fermentation performance of the overexpression of different combinations of enzymes of the phosphoketolase-phosphotransacetylase-acetaldehyde dehydrogenase pathway in TMB3001c (control) and TMB3111c (Δald6). The shown physiological parameters refer to the xylose consumption phase of anaerobic batch cultures on 50 g/l glucose and 50 g/l xylose, after glucose depletion.

Both pathways result in an extra molecule of acetaldehyde. FIG. 5 shows cultivation profiles of xylose fermentations of *S. cerevisiae* TMB 3001 (containing the genes XR, XDH, and XK) (Eliasson et al, 2000). The fermentations were carried out in a 3 l New Brunswick Bioflo III fermentor (New Brunswick Scientific Co., Edison, N.J., USA) at pH 5.5 and T=30 degrees. The medium consisted of 20 g/l of glucose, and 50 g/l of xylose plus mineral salts, trace elements, vitamins and ergosterol/TWEEN (Verduyn et al, 1990). To obtain anaerobic conditions the fermentor was continuously sparged with nitrogen at a rate of 0.2 l/min. It can be seen that the yield of ethanol is very low, about 0.13 g/g of xylose and most of the xylose ends up in xylitol. In FIG. 5-*acetaldehyde* has been continuously fed to the fermentor at a low rate. In this case no xylitol is formed and the ethanol production yield increases significantly. This indicates that the extra produced acetaldehyde from pathways 1 and 2 above can solve the xylitol secretion problem.

FIG. 5 thus shows xylose fermentation with and without acetaldehyde addition.

As a conclusion it can be stated that xylitol and also glycerol by-product formation would be prevented if enzymatic activities for phosphoketolase, phosphate acetyl transferase and acetaldehyde dehydrogenase (acylating) were introduced in *S. cerevisiae*. In such a hypothetical pathway, excessive NADH formed either from xylitol oxidation or amino acid synthesis would be regenerated to $NAD^+$ by converting acetyl-phosphate, formed in the phosphoketolase reaction, to ethanol using phosphate acetyl transferase, acetaldehyde dehydrogenase (acylating) and alcohol dehydrogenase.

Random mutagenesis was successfully used to develop the recombinant *S. cerevisiae* TMB 3400 that has a maximum specific growth rate of 0.14 $h^{-1}$ on xylose, compared to 0.025 $h^{-1}$ for its parental strain, the non-mutated, recombinant *S. cerevisiae* TMB 3399. *S. cerevisiae* TMB 3400 showed elevated mRNA expression levels of (i) HXT5, encoding a hexose transporter, (ii) XKS1, encoding xylulokinase, an enzyme involved in one of the initial steps of xylose utilisation, and (iii) SOL3, GND1, TAL1 and TKL1, encoding enzymes in the pentose phosphate pathway. The biomass yield of *S. cerevisiae* TMB 3400 on xylose, 0.43 g biomass g xylose$^{-1}$ was lower than that on glucose, 0.47 g biomass g xylose$^{-1}$.

Establishment of the novel fermentation pathway to ethanol: the phosphoketolase-phosphotransacetylase-acetaldehyde dehydrogenase pathway.

Since more than a decade, metabolic engineering strategies were applied to improve ethanol production efficiency from xylose fermentation with *S. cerevisiae*. Different rational and evolutionary approaches resulted either in improved ethanol yields (Jeppsson et al. 2002a) or in improved xylose fermentation rates (Aristidou et al. 1999), but generally never in a simultaneous significant increase of both physiological parameters. To achieve ethanol productivities on xylose comparable as on glucose, both, improved fermentation rate and yield, are needed. In this framework, the phosphoketolase-phosphotransacetylase-acetaldehyde dehydrogenase pathway could offer a new opportunity to reach a milestone in xylose fermentation efficiency improvement. This pathway is widely used by heterofermentative lactic acid bacteria, converting first xylulose 5-phosphate to acetyl phosphate and glyceraldehyde phosphate, then acetyl phosphate to acetyl-CoA, which is finally reduced to acetaldehyde (FIG. 5). In anaerobic yeast xylose catabolism, this pathway could provide an alternative opportunity to re-oxidize surplus NADH, channeling carbon flux to ethanol production, if supported by a deletion of the constitutive, cytosolic and NADP dependent aldehyde dehydrogenase (ald6). Together with the consequent decreased xylitol and glycerol accumulation, the bypass of the $CO_2$ producing pyruvate decarboxylase reaction could potentially increase both effective and theoretical ethanol yields.

To establish a functional phosphoketolase-phosphotransacetylase-acetaldehyde dehydrogenase pathway in S. cerevisiae, we analyzed the overexpression of the Bifidobacterium lactis phosphoketolase (xfp), the Bacillus subtilis phosphotransacetylase (pta), and the Entamoeba histolytica acetaldehyde dehydrogenase (Ehadh2) in presence or absence of a deletion of the cytosolic and constitutive aldehyde dehydrogenase (ald6) in S. cerevisiae TMB3001.

Materials and Methods

Strains and Media

The present experiments were inoculated with the recombinant S. cerevisiae strain TMB3001 (CEN.PK 113-7A (MATa, his3-Δ1, MAL2-8c, SUC2) his3: YIpXR/XDH/XK), which contains the entire xylose-utilization pathway (Eliasson et al. 2000). Overexpression of XR is controlled by the alcohol dehydrogenase promoter and terminator, whereas XDH and XK are both under the control of phosphoglycerate kinase promoters and terminators. Rational metabolic engineering experiments on the establishment of the phosphoketolase-phosphotransacetylase-acetaldehyde dehydrogenase pathway in yeast were performed with the TMB3001c strain (CEN.PK2-1C (MATa; ura3-52; trp1-289; leu2-3, 112; his3-Δ1, MAL2-8c, SUC2) his3:YIpXR/XDH/XK).

For physiological analysis and evolution experiments, yeast cultures were grown at 30° C. in minimal medium containing per liter: 5 g $(NH_4)_2SO_4$, 3 g $KH_2PO_4$, 0.5 g $MgSO_4.7H_2O$, 15 mg EDTA, 4.5 mg $ZnSO_4.7H_2O$, 0.3 mg $CoCl_2.6H_2O$, 1 mg $MnCl_2.4H_2O$, 0.3 mg $CuSO_4.4H_2O$, 4.5 mg $CaCl_2.2H_2O$, 3 mg $FeSO_4.7H_2O$, 0.4 mg $Na_2MoO_4.2H_2O$, 1 mg $H_3BO_3$, 0.1 mg KI, 0.05 mg biotin, 1 mg Ca pantothenate, 1 mg nicotinic acid, 25 mg inositol, 1 mg thiamine HCl, 1 mg pyridoxine HCl, and 0.2 mg para-aminobenzoic acid (pH 5.0) (Verduyn et al. 1992). In chemostat cultures, 0.1 g $l^{-1}$ polypropylene glycol P 2000 was added to prevent foam formation. The medium was supplemented with ergosterol (Fluka) and Tween 80 (Sigma) for anaerobic cultivation. Both components were dissolved in boiling 99.8% (v/v) ethanol and were added to the medium at a final concentration of 0.01 g $l^{-1}$ and 0.42 g $l^{-1}$, respectively. Solid media were prepared by adding 1.5% (w/v) technical Agar (Becton Dickinson). For anaerobic growth on xylose plates, population aliquots were washed twice with PBS (8 g $l^{-1}$NaCl, 0.2 g $l^{-1}$ KCl, 1.44 g $l^{-1}$ $Na_2HPO_4$, 0.24 g $l^{-1}$ $KH_2PO_4$, pH 7.0) and plated on anaerobic minimal medium containing 20 g $l^{-1}$ xylose as the sole carbon source. Plates were incubated at 30° C. in sealed jars, using the GasPack Plus system (Becton Dickinson) to provide an anaerobic atmosphere, which was verified by indicator strips (Becton Dickinson).

Cloning and Yeast Transformation Procedures

Standard molecular biology techniques were used to clone the phosphoketolase (xfp), the phosphotransacetylase (pta) and the acetaldehyde dehydrogenase (Ehadh2) genes under the strong truncated HXT7 promotor in the yeast multicopy plasmids p426HXT7, p424HXT7 and p425HXT7 (Hauf 1998), respectively. The Bifidobacterium lactis xfp gene was sub-cloned by ligation of the 2.6 kbp DNA fragment, resulting from the EcoRI-HindIII digestion of the pFPK6 plasmid (Meile et al. 2001), after gel extraction (QUIAEX II, QUIAGEN, Basel, Switzerland). Analogously, the Entamoeba histolytica Ehadh2 containing 3 kbp cDNA fragment was sub-cloned from the BamHI-XbaI digestion of pET3a-ehadh2 (Yong et al. 1996) into the BamHI-SpeI digested p425HXT7 plasmid. The Bacillus subtilis pta gene was amplified with taq DNA polymerase (Promega, Madison, Wis.) by PCR (Cycle: 1×2 min. at 95° C.; 30×(1 min at 95° C., 0.5 min at 58° C., 1.25 min at 74° C.); 5 min at 74° C.) from B. subtilis genomic DNA using the following primers:
Fwd: 5'-cgg gat cca tgg cag att tat ttt caa cag tg-3';
Rev: 5'-cca tcg atg tcg aga gct gcc att gtc tcc-3'.
This Fragment was ligated using the BamHI-ClaI restriction sites of p424HXT7.

Plasmids were transformed in S. cerevisiae by the lithium acetate method using the S.c. EasyComp transformation kit (Invitrogen, Carlsbad, Calif.).

Deletion of ald6

The KanMX cassette with the 500 bp upstream and the 500 bp downstream flanking regions of the ald6 ORF was obtained from the S. cerevisiae Y02767 (BY4741; MATa; his3Δ1; leu2Δ0; met15Δ0; ura3Δ0; YPL061w::kanMX4) (Euroscarf, Frankfurt, Germany) chromosomal DNA by PCR (Cycle: 1×5 min at 94° C.; 40× (0.5 min at 94° C.; 1 min at 52° C.; 2.83 min at 72° C.); 10 min at 72° C.) using oligonucleotides
5'-gac aaa aga aaa acg acc gaa aag g-3' and
5'-ata tga tct ctg atg gcg aaa tgg-3'.

The PCR product was transformed by the lithium acetate method in TMB3001c generating TMB3111c by selection for homologous recombination on YPD plates containing geneticin (300 μg/ml). Deletion of ald6 was checked by PCR with the same primers used to generate the DNA fragment and two KanMX internal primers:
5'-tga ttt tga tga cga gcg taa t-3' and
5'-ctg cag cga gga gcc gta at-3'.

The phosphoketolase-phosphotransacetylase-acetaldehyde dehydrogenase pathway. To evaluate the feasibility of the establishment of the phosphoketolase-phosphotransacetylase-acetaldehyde dehydrogenase pathway in S. cerevisiae, and to investigate its effect on xylose fermentation, we analyzed the overexpression of different combinations of xfp, pta and Ehadh2 in TMB3001c and TMB3111c on xylose fermentation performance. Physiological data were determined during xylose consumption phase of an anaerobic batch culture grown on 50 g/l glucose and 50 g/l xylose minimal medium, after glucose depletion (FIG. 5). Overexpression of the acetaldehyde dehydrogenase alone or in combination with the phosphotransacetylase, both in an aldehyde dehydrogenase (ald6) deletion background show the best improvements in ethanol yield (up to more than 30%) and specific xylose uptake rate (up to 75%). Furthermore, overexpression of the phosphoketolase enzyme seems not to be necessary to achieve the latter improvements, but has a rather negative effect, increasing acetate production also in the aldehyde dehydrogenase deletion strain. Nevertheless, the latter strain shows in general a significantly decreased acetate yield.

Remarkably, such metabolically engineered strains have up to doubled specific xylose consumption rates and up to 40% increased ethanol yields on xylose. Since up to date almost all successful metabolic engineering strategies resulted in either higher yield or higher rate, these last results clearly indicate the importance of the new engineering strategy.

FIGURE LEGENDS

A) specific xylose uptake rate ■;
B) Ethanol □ and acetate ■ yields on xylose;
C) Xylitol ▨ and glycerol ▨ yields on xylose.

REFERENCES

Aarnio, T. H., Sulhko, M. L. and Kauppinen, V. S. (1991). Isolation of acetic acid-tolerant bakers yeast variants in a turbidostat. *Appl Biochem Biotechnol* 27, 55-64.

Amore, R., Wilhelm, M. and Hollenberg, C. P. (1989). The fermentation of xylose—an analysis of the expression of *Bacillus* and *Actinoplanes* xylose isomerase genes in yeast. *Appl. Microbiol. Biotechnol.* 30, 351-357.

Anderlund, M., Nissen, T. L., Nielsen, J., Villadsen, J., Rydstrom, J., Hahn-Hägerdal, B. and Kielland-Brandt, M. C. (1999).

Expression of the *Escherichia coli* pntA and pntB genes, encoding nicotinamide nucleotide transhydrogenase, in *Saccharomyces cerevisiae* and its effect on product formation during anaerobic glucose fermentation. *Appl Environ Microbiol* 65, 2333-40.

Andreasen, A. A. and Stier, T. J. B. (1953). Anaerobic nutrition of *Saccharomyces* cerevisiae. I. Ergosterol requirement for growth in a defined medium. *J Cell Comp Physiol* 41, 23-36.

Andreasen, A. A. and Stier, T. J. B. (1954). Anaerobic nutrition of *Saccharomyces cerevisiae*. II. Unsaturated fatty acid requirement for growth in a defined medium. *J Cell Comp Physiol* 43, 271-281.

Bailey, J. E. (1991). Toward a science of metabolic engineering. *Science* 252, 1668-75.

Bailey, J. E., Sburiati, A., Hatzimanikatis, V., Lee, K., Renner, W. A. and Tsai, P. S. (1996). Inverse metabolic engineering: A strategy for directed genetic engineering of useful phenotypes. *Biotechnol Bioeng* 52, 109-121.

Batt, C. A., Carvallo, S., Easson, D. D., Jr Akedo, M. and Sinskey, A. J. (1986). Direct evidence for a xylose metabolic pathway in *Saccharomyces cerevisiae*. *Biotechnol Bioeng* 28, 549-553.

Börling, T. and Lindman, B. (1989). Evaluation of xylose-fermenting yeasts for ethanol production from spent sulfite liqor. *Enzyme Microb Technol* 11, 240-246.

Boles, E., Heinisch, J. and Zimmermann, F. K. (1993). Different signals control the activation of glycolysis in the yeast *Saccharomyces cerevisiae*. *Yeast* 9, 761-70.

Bolotin, A., Wincker, P., Mauger, S., Jaillon, O., Malarme, K., Weissenbach, J., Ehrlich, S. D. and Sorokin, A. (2001). The complete genome sequence of the lactic add bacterium *Lactococcus lactis* ssp. lactis IL1403. *Genome Res* 11, 731-53.

Bothast, R. J., Nichols, N. N. and Dien, B. S. (1999). Fermentations with new recombinant organisms. *Biotechnol Prog* 15, 867-75.

Brown, C. J., Todd, K. M. and Rosenzweig, R. F. (1998). Multiple duplications of yeast hexose transport genes in response to selection in a glucose-limited environment. *Mol Biol Evol* 15, 931-42.

Brown, S. W. and Oliver, S. G. (1982). Isolation of ethanol-tolerant mutants of yeast by continuous selection. *Eur J Appl Microbiol Biotechnol* 16, 119-122.

Bruinenberg, P. M., de Bot, P. H. M., van Dijken, J. P. and Scheffers, W. A. (1983). The role of redox balances in the anaerobic fermentation of xylose by yeasts. *Eur J Appl Microbiol Biotechnol* 18, 287-292.

Bruinenberg, P. M., De Bot, P. H. M., van Dijken, J. P. and Scheffers, W. A. (1984). Nadh-linked aldose reductase the key to anaerobic alcoholic fermentation of xylose by yeasts. *Appl Microbiol Biotechnol* 19, 256-260.

Burton, K. (1974). The enthalpy change for the reduction of nicotinamide—adenine dinucleotide. *Biochem J* 143, 365-8.

Busturia, A. and Lagunas, R. (1986). Catabolite inactivation of the glucose transport system in *Saccharomyces cerevisiae*. *J Gen Microbiol* 132, 379-85.

Butler, P. R., Brown, M. and Oliver, S. G. (1996). Improvement of antibiotic titers from *Streptomyces* bacteria by interactive continuous selection. *Biotechnol Bioeng* 49, 185-196.

Bär, J., Naumann, M., Reuter, R. and Kopperschläger, G. (1996). Improved purification of ribulose 5-phosphate 3-epimerase from *Saccharomyces cerevisiae* and characterization of the enzyme. *Bioseparation* 6, 233-41.

Cameron, D.C. and Tong, I. T. (1993). Cellular and metabolic engineering. An overview. *Appl Biochem Biotechnol* 38, 105-40.

Chiang, C. and Knight, S. G. (1960). Metabolism of D-xylose by moulds. *Nature* 188, 79-81.

Chiang, L. C., Gong, C. S., Chen, L. F. and Tsao, G. T. (1981). D-xylulose fermentation to ethanol by *Saccharomyces cerevisiae*. *Appl Environ Microbiol* 42, 284-289.

Cirillo, V. P. (1968). Relationship between sugar structure and competition for the sugar transport system in Bakers' yeast. *J Bacteriol* 95, 603-11.

De Virgilio, C., Burckert, N., Barth, G., Neuhaus, J. M., Boller, T. and Wiemken, A. (1992). Cloning and disruption of a gene required for growth on acetate but not on ethanol: the acetyl-coenzyme A synthetase gene of *Saccharomyces cerevisiae*. *Yeast* 8, 1043-51.

Ellasson, A. (2001). Ethanol production by recombinant and natural xylose-utilising yeasts, *Department of Applied Microbiology*, Lund University.

Eliasson, A., Hofmeyr, J.-H. S., Pedler, S. and Hahn-Hägerdal, B. (2001). The xylose reductase/xylitol dehydrogenase/xylulokinase ratio affects product formation in recombinant xylose-utilising *Saccharomyces cerevisiae*. *Enzyme Microb Technol* 29, 288-297.

Evans, C. T. and Ratledge, C. (1984). Induction of xylulose-5-phosphate phosphoketolase in a variety of yeasts grown on D-xylose: the key to efficient xylose metabolism. *Arch Microbiol* 139, 48-52.

Fell, D. A. and Thomas, S. (1995). Physiological control of metabolic flux: the requirement for multisite modulation. *Biochem J* 311, 35-9.

Ferrari, M. D., Neirotti, E., Albornoz, C. and Saucedo, E. (1992). Ethanol production from eucalyptus wood hemicellulose hydrolysate by *Pichia stipitis*. *Biotechnol Bioeng* 40, 753-759.

Gong, C. S., McCracken, L. D. and Tsao, G. T. (1981). Direct fermentation of D-xylose to ethanol by a xylose fermenting yeast mutant *Candida*-sp XF-217. *Biotechnol Lett* 3, 245-250.

Hahn-Hägerdal, B., Wahlborn, C. F., Gardonyl, M., van Zyl, W. H., Cordero Otero, R. R. and Jönsson, L. J. (2001). Metabolic engineering of *Saccharomyces cerevisiae* for xylose utilization. *Adv Biochem Eng Biotechnol* 73, 53-84.

Hall, B. G., Yokoyama, S. and Calhoun, D. H. (1983). Role of cryptic genes in microbial evolution. *Mol Biol Evol* 1, 109-24.

Hallborn, J., Walfridsson, M., Airaksinen, U., Ojamo, H., Hahn-Hägerdal, B., Penttilä, M. and Keränen, S. (1991). Xylitol production by recombinant *Saccharomyces cerevisiae*. *Biotechnology* (N Y) 9, 1090-5.

Hauf, J., Zimmermann, F. K. and Müller, S. (2000). Simultaneous genomic overexpression of seven glycolytic enzymes in the yeast *saccharomyces cerevisiae*. *Enzyme Microb Technol* 26, 688-698.

Hinman, N. D., Wright, 3. D., Hoagland, W. and Wyman, C. E. (1989). Xylose fermentation. An economic analysis. *Appl Biochem Biotechnol* 20/21, 391-401.

Ho, N. W. and Chang, S. F. (1989). Cloning of yeast xylulokinase gene by complementation of *Escherichia coli* and yeast mutations. *Enzyme Microb Technol* 11, 417-421.

Ho, N. W. Y., Stevis, P., Rosenfeld, S., Huang, J. J. and Tsao, G. T. (1983). Expression of the *Escherichia coli* isomerase gene by a yeast promoter. *Biotechnol. Bioeng. Symp.* 13, 245-250.

Hochster, R. M. and Watson, R. W. (1954). Enzymatic Isomerization of D-xylose to D-xylulose. *Arch Biochem Biophys* 48, 120-129.

Jeffries, T. W. (1984). Mutants of *Pachysolen tannophilus* showing enhanced rates of growth and ethanol formation from D-xylose. *Enzyme Micrbiol Technol* 6, 254-258.

Johansson, B. (2001). Metabolic engineering of the pentose phosphate pathway of xylose fermenting *Saccharomyces cerevisiae, Department of Applied Microbiology*, Lund, University.

Jones, E. W. and Fink, G. R. (1982). Regulation of amino acids and nucleotide biosynthesis in yeast in Strathern, J. N., Jones, E. W. and Broach, J. R. (Eds), *The molecular biology of the yeast Saccharomyces, Metabolism and gene expression*, Cold Spring Harbor Laboratory, pp. 181-300.

Jones, R. P. (1989). Biological principles for the effects of ethanol. *Enzyme Microbiol Technol* 11, 130-153.

Kiely, M. E., Stuart, A. L. and Wood, T. (1973). Partial purification and kinetic properties of ribose-5-phosphate ketol-isomerase and ribulose-5-phosphate 3-epimerase from various sources. *Biochim Biophys Acta* 293, 534-41.

Kolot, F. B. (1980). New trends in yeast biotechnology-immobilised cells. *Process Biochem* 15, 2-8.

Kommunikationskommitën (1996). Betänkande av Alternativbränsleutredningen SOU 1996:184.

Kostrzynska, M., Sopher, C. R. and Lee, H. (1998). Mutational analysis of the role of the conserved lysine-270 in the *Pichia stipitis* xylose reductase. *FEMS Microbiol Lett* 159, 107-12.

Kotyk, A. (1967). Properties of the sugar carrier in baker's yeast. II. Specificity of transport. *Folia Microbiol* 12, 121-31.

Kuhn, A., van Zyl, C., van Tonder, A. and Prior, B. A. (1995). Purification and partial characterization of an aldo-keto reductase from *Saccharomyces cerevisiae*. *Appl Environ Microbiol* 61, 1580-5.

Kötter, P. and Ciriacy, M. (1993). Xylose fermentation by *Saccharomyces cerevisiae*. *Appl Microbiol Biotechnol* 38, 776-783.

Larsson, S., Palmqvist, E., Hahn-Hägerdal, B., Tengborg, C., Stenberg, K., Zacchi, G. and Nilvebrant, N. O. (1999). The generation of fermentation inhibitors during dilute acid hydrolysis of softwood. *Enzyme Microb Technol* 24, 151-159.

Lighthelm, M. E., Prior, B. A., du Preez, J. C. and Brandt, V. (1988). An investigation of carbon-13 D-xylose metabolism in *Pichia stipitis* under aerobic and anaerobic conditions. *Appl Microbiol Biotechnol* 28, 293-296.

Ligthelm, M. E., Prior, B. A. and du Preez, J. C. (1989). Effect of hydrogen acceptors on D-xylose fermentation by anaerobic culture of immobilized *Pachysolen tannophilus* cells. *Biotechnol Bioeng* 32, 839-844.

Loveless, A. (1969). Possible relevance of 0-6 alkylation of deoxyguanosine to the mutagenicity and carcinogenicity of nitrosamines and nitrosamides. *Nature* 223, 206-7.

Mavrovouniotis, M. L. (1993). Identification of localized and distributed bottlenecks in metabolic pathways. *Ismb* 1, 275-83.

Meile, L., Rohr, L. M., Geissmann, T. A., Herensperger, M. and Teuber, M. (2001). Characterization of the D-xylulose 5-phosphate/D-fructose 6-phosphate phosphoketolase gene (xfp) from *Bifidobacterium lactis*. *J Bacteriol* 183, 2929-36.

Metzger, M. H. and Hollenberg, C. P. (1995). Amino acid substitutions in the yeast *Pichia stipitis* xylitol dehydrogenase coenzyme-binding domain affect the coenzyme specificity. *Eur J Biochem* 228, 50-4.

Moes, C. J., Pretorius, I. S. and Zyl, W. H. v. (1996). Cloning and expression of the *Clostridium thermosulfurogenes* D-xylose isomerase gene (xylA) in *Saccharomyces cerevisiae*. *Biotechnol Lett* 18, 269-274.

Moniruzzaman, M., Dien, B. S., Ferrer, B., Hespell, R. B., Dale, B. E., Ingram, L. O. and Bothast, R. J. (1996). Ethanol production from AFEX pretreated corn fiber by recombinant bacteria. *Biotechnol Lett* 18, 985-990.

Müler, S., Boles, E., May, M. and Zimmermann, F. K. (1995). Different internal metabolites trigger the induction of glycolytic gene expression in *Saccharomyces cerevisiae*. *J Bacteriol* 177, 4517-9.

Mumberg, D., Muller, R. and Funk, M. (1995). Yeast vectors for the controlled expression of heterologous proteins in different genetic backgrounds. *Gene* 156, 119-22.

Neuhauser, W., Haltrich, D., Kulbe, K. D. and Nidetzky, B. (1997). NAD(P)H-dependent aldose reductase from the xylose-assimilating yeast *Candida tenuis*. Isolation, characterization and biochemical properties of the enzyme. *Biochem J* 326, 683-92.

Nielsen, J. (1998). Metabolic engineering: techniques for analysis of targets for genetic manipulations. *Biotechnol Bioeng* 58, 125-32.

Nielsen, J. (2001). Metabolic engineering. *Appl Microbiol Biotechnol* 55, 263-83.

Nielsen, J. and Villadsen, J. (1994). *Bioreaction engineering principles*. Plenum Press.

Olsson, L. and Hahn-Hägerdal, B. (1993). Fermentative performance of bacteria and yeasts in lignocellulose hydrolysates. *Proc Biochem* 28, 249-257.

Ostergaard, S., Olsson, L., Johnston, M. and Nielsen, J. (2000). Increasing galactose consumption by *Saccharomyces cerevisiae* through metabolic engineering of the GAL gene regulatory network. *Nat Biotechnol* 18, 1283-6.

Palmqvist, E. and Hahn-Hägerdal, B. (2000a). Fermentation of lignocellulosic hydrolysates. I: inhibiton and detoxification. *Biores Technol* 74, 17-24.

Palmqvist, E. and Hahn-Hägerdal, B. (2000b). Fermentation of lignocellulosic hydrolysates. II: inhibitors and mechanisms of inhibition. *Biores Technol* 74, 25-33.

Parekh, S., Vinci, V. A. and Strobel, R. J. (2000). Improvement of microbial strains and fermentation processes. *Appl Microbiol Biotechnol* 54, 287-301.

Rado, T. A. and Hoch, J. A. (1973). Phosphotransacetylase from *Bacillus subtilis*: purification and physiological studies. *Biochim Biophys Acta* 321, 114-25.

Ratledge, C. and Holdsworth, J. E. (1985). Properties of a pentulose-5-phosphate phosphoketolase from yeasts grown on xylose. *Appl Microbiol Biotechnol* 22, 217-221.

Richard, P., Tolvari, M. H. and Penttilä, M. (1999). Evidence that the gene YLR070c of *Saccharomyces cerevisiae* encodes a xylitol dehydrogenase. *FEBS Lett* 457, 135-8.

Rizzi, M., Erlemann, P., Bui-Thanh, N. A. and Dellweg, H. (1988). Xylose fermentation by yeasts 4. Purification and kinetic studies of xylose reductase from *Pichia stipitis*. *Appl Microbiol Biotechnol* 29, 148-154.

Rizzi, M., Harwart, K., Bul-Thanh, N. A. and Dellweg, H. (1989a). A kinetic study of the NAD-xylitol dehydrogenase from the yeast *Pichia stipitis*. *J Ferment Bioeng* 67, 25-30.

Rizzi, M., Harwart, K., Erlemann, P., Bul-Thanh, N. A. and Dellweg, H. (1989b). Purification and properties of the NAD-xylitol dehydrogenase from the yeast *Pichia stipitis*. *J Ferment Bioeng* 67, 20-24.

Rodriguez-Pena, J. M., Cid, V. J., Arroyo, J. and Nombela, C. (1998). The YGR194c (XKS1) gene encodes the xylulokinase from the budding yeast *Saccharomyces cerevisiae*. *FEMS Microbiol Lett* 162, 155-60.

Saddler, J. N., Ramos, L. P. and Breuil, C. (1993). Steam pretreatment of lignocellulosic residues in Saddler, J. N. (Ed), *Bioconversion of forest and agricultural plant residues*, CAB International, pp. 73.

Sanchez, B. and Bautista, J. (1988). Effects of furfural and 5-hydroxymethylfurfural on the fermentation of *Saccharomyces cerevisiae* and biomass production from *Candida guilliermondii*. *Enzyme Microb Technol* 10, 315-318.

Sarthy, A. V., McConaughy, B. L., Lobo, Z., Sundstrom, J. A., Furlong, C. E. and Hall, B. D. (1987). Expression of the *Escherichia coli* xylose isomerase gene in *Saccharomyces cerevisiae*. *Appl Environ Microbiol* 53, 1996-2000.

Sauer, U. (2001). Evolutionary engineering of industrially important microbial phenotypes. *Adv Biochem Eng Biotechnol* 73, 129-69.

Schaaff, I., Heinisch, J. and Zimmermann, F. K. (1989). Overproduction of glycolytic enzymes in yeast. *Yeast* 5, 285-90.

Sega, G. A. (1984). A review of the genetic effects of ethyl methanesulfonate. *Mutat Res* 134, 113-42.

Skoog, K. and Hahn-Hägerdal, B. (1988). Xylose fermentation. *Enzyme Microb Technol* 10, 66-80.

Skoog, K. and Hahn-Hägerdal, H. (1990). Effect of oxygenation on xylose fermentation by *Pichia stipitis*. *Appl Environ Microbiol* 56, 3389-3394.

Stenberg, K., Tengborg, C., Galbe, M. and Zacchi, G. (1998). Optimisation of steam pretreatment of SO2-imprignated mixed softwoods for ethanol production. *J Chem Technol Biotechnol* 71, 299-308.

Stephanopoulos, G. (1994). Metabolic engineering. *Curr Opin Biotechnol* 5, 196-200.

Stephanopoulos, G. (1999). Metabolic fluxes and metabolic engineering. *Metab Eng* 1, 1-11.

Taherzadeh, M. J., Eklund, R., Gustafsson, L., Niklasson, C. and Lidún, G. (1997). Characterization and fermentation of dilute-acid hydrolysates from wood. *Ind Eng Chem Res* 36, 4659-4665.

Taherzadeh, M. J., Niklasson, C. and Lidén, G. (1999). Conversion of dilute-acid hydrolyzates of spruce and birch to ethanol by fed-batch fermentation. *Biores Technol* 69, 59-66.

Tantirungklj, M., Nakashima, N., Seki, T. and Yoshida, T. (1993). Construction of xylose-assimilating *Saccharomyces cerevisiae*. *J Ferm Bioeng* 75, 83-88.

Tantirungkij, M., Izuishi, T., Seki, T. and Yoshida, T. (1994). Fed-batch fermentation of xylose by a fast-growing mutant of xylose-assimilating recombinant *Saccharomyces cerevisiae*. *Appl Microbiol Biotechnol* 41, 8-12.

Tengborg, C., Stenberg, K., Galbe, M., Zacchi, G., Larsson, S., Palmqvist, E. and Hahn-Hägerdal, B. (1998). Comparison of $SO_2$ and $H_2SO_4$ impregnation of softwood prior to steam pretreatment on ethanol production. *Appl Biochem Biotechnol* 70-72, 3-15.

Thauer, R. K., Jungermann, K. and Decker, K. (1977). Energy conservation in chemotrophic anaerobic bacteria. *Bacteriol Rev* 41, 100-80.

Toth, J., Ismaiel, A. A. and Chen, J. S. (1999). The aid gene, encoding a coenzyme A-acylating aldehyde dehydrogenase, distinguishes *Clostridium beijernckii* and two other solvent-producing clostridia from *Clostridium acetobutylicum*. *Appl Environ Microbiol* 65, 4973-80.

Walfridsson, M., Anderlund, M., Bao, X. and Hahn-Hägerdal, B. (1997). Expression of different levels of enzymes from the *Pichia stipitis* XYL1 and XYL2 genes in *Saccharomyces cerevisiae* and its effects on product formation during xylose utilisation. *Appl Microbiol Biotechnol* 48, 218-24.

Walfridsson, M., Bao, X., Anderlund, M., Lilius, G., Bülow, L. and Hahn-Hägerdal, B. (1996). Ethanolic fermentation of xylose with *Saccharomyces cerevisiae* harboring the *Thermus thermophilus* xylA gene, which expresses an active xylose (glucose) isomerase. *Appl Environ Microbiol* 62, 4648-51.

Walfridsson, M., Hallborn, J., Penttilä, M., Keränen, S. and Hahn-Hägerdal, B. (1995). Xylose-metabolizing *Saccharomyces cerevisiae* strains overexpressing the TKL1 and TAL1 genes encoding the pentose phosphate pathway enzymes transketolase and transaldolase. *Appl Environ Microbiol* 61, 4184-4190.

Van den Berg, M. A. and Steensma, H. Y. (1995). ACS2, a *Saccharomyces cerevisiae* gene encoding acetyl-coenzyme A synthetase, essential for growth on glucose. *Eur J Biochem* 231, 704-13.

van der Westhuizen, T. J. and Pretorius, I. S. (1992). The value of electrophoretic fingerprinting and karyotyping in wine yeast breeding programmes. *Antonie Van Leeuwenhoek* 61, 249-257.

van Zyl, C., Prior, B. A., Kilian, S. G. and Brandt, E. V. (1993). Role of D-ribose as a cometabolite in D-xylose metabolism by *Saccharomyces cerevisiae*. *Appl Environ Microbiol* 59, 1487-1494.

van Zyl, C., Prior, B. A., Kilian, S. G. and Kock, J. L. (1989). D-xylose utilization by *Saccharomyces cerevisiae*. *J Gen Microbiol* 135, 2791-8.

VanCauwenberge, 1. E., Bolen, P. L., McCracken, D. A. and Bothast, R. J. (1989). Effect of growth conditions on cofactor-linked xylose reductase activity in *Pachysolen tannophilus*. *Enzyme Microb Technol* 11, 662-667.

Wang, P. Y. and Schneider, H. (1980). Growth of yeasts on D-xylulose. *Can J Microbiol* 26, 1165-8.

Webb, S. R. and Lee, H. (1992). Characterization of xylose reductase from the yeast *Pichia stipitis*: Evidence for functional thiol and histidyl groups. *J Gen Microbiol* 138, 1857-1863.

Verduyn, C., Frank, J., van Dijken, J. P. and Scheffers, W. A. (1985a). Multiple forms of xylose reductase in *Pachysolen tannophilus* CBS4044. *FEMS Microbiol Lett* 30, 313-317.

Verduyn, C., Postma, E., Scheffers, W. A. and van Dijken, J. P. (1990). Physiology of *Saccharomyces cerevisiae* in anaerobic glucose-limited chemostat cultures. *J Gen Microbiol* 136, 395-403.

Verduyn, C., van Kleef, R., Frank, J., Schreuder, H., van Dijken, J. P. and Scheffers, W. A. (1985b). Properties of the NAD(P)H-dependent xylose reductase from the xylose-fermenting yeast *Pichia stipitis*. *Biochem J* 226, 669-77.

Whitworth, D. A. and Ratledge, C. (1977). Phosphoketolase in *Rhodotorula graminis* and other yeasts. *J Gen Microbiol* 102, 397-401.

Visser, W., Scheffers, W. A., Batenburg-van der Vegte, W. H. and van Dijken, J. P. (1990). Oxygen requirements of yeasts. *Appl Environ Microbiol* 56, 3785-92.

Wloch, D. M., Szafraniec, K., Borts, R. H. and Korona, R. (2001). Direct estimate of the mutation rate and the distribution of fitness effects in the yeast *Saccharomyces cerevisiae*. *Genetics* 159, 441-52.

Wodicka, L., Dong, H., Mittmann, M., Ho, M. H. and Lockhart, D. J. (1997). Genome-wide expression monitoring in *Saccharomyces cerevisiae*. *Nat Biotechnol* 15, 1359-67.

von Sivers, M. and Zacchi, G. (1996). Ethanol from lignocellulosics: a review of the economy. *Biores Technol* 56, 131-140.

Zeyl, C. and DeVisser, J. A. (2001). Estimates of the rate and distribution of fitness effects of spontaneous mutation in *Saccharomyces cerevisiae*. *Genetics* 157, 53-61.

Zhang, Y. and Lee, H. (1997). Site-directed mutagenesis of the cysteine residues in the *Pichia stipitis* xylose reductase. *FEMS Microbiol Lett* 147, 227-32.

The invention claimed is:

1. A method for preparing an ethanol producing, xylose utilizing strain of *Saccharomyces cerevisiae* comprising introducing and overexpressing a xylose reductase gene, a xylitol dehydrogenase gene, a xylulokinase gene, a *Bacillus subtilis* phosphoacetyltransferase gene, and an *Entamoeba histolytica* aldehyde dehydrogenase gene in a *Saccharomyces cerevisiae* strain, wherein said *Saccharomyces cerevisiae* strain comprises a deletion of the endogenous aldehyde dehydrogenase (ald6) gene.

2. The method according to claim 1, wherein a gene for production of phosphoketolase is further introduced, and optionally overexpressed.

3. The method according to, claim 2, wherein the gene encoding phosphoketolase is cloned from any heterofermentative lactic acid bacterium selected from the group consisting of *Lactobacillus pentosus, Lactobacillus plantarum*, and *Leuconstoc mesenteroides*.

* * * * *